(12) United States Patent
Papac et al.

(10) Patent No.: US 9,844,319 B2
(45) Date of Patent: Dec. 19, 2017

(54) OPTICAL COHERENCE TOMOGRAPHY GUIDED EPIRETINAL MEMBRANE PEELING

(71) Applicant: NOVARTIS AG, Basel (CH)

(72) Inventors: Michael J. Papac, North Tustin, CA (US); Hugang Ren, Irvine, CA (US); Lingfeng Yu, Rancho Santa Margarita, CA (US)

(73) Assignee: Novartis AG, Basel (CH)

( * ) Notice: Subject to any disclaimer, the term of this patent is extended or adjusted under 35 U.S.C. 154(b) by 108 days.

(21) Appl. No.: 14/837,341

(22) Filed: Aug. 27, 2015

(65) Prior Publication Data

US 2017/0055828 A1 Mar. 2, 2017

(51) Int. Cl.
| | |
|---|---|
| *A61B 3/14* | (2006.01) |
| *A61B 3/00* | (2006.01) |
| *A61B 3/10* | (2006.01) |
| *A61B 90/00* | (2016.01) |
| *A61B 3/12* | (2006.01) |
| *A61B 3/13* | (2006.01) |
| *A61F 9/007* | (2006.01) |
| *G02B 27/01* | (2006.01) |
| *A61F 9/008* | (2006.01) |

(52) U.S. Cl.
CPC ............ *A61B 3/102* (2013.01); *A61B 3/0025* (2013.01); *A61B 3/0058* (2013.01); *A61B 3/12* (2013.01); *A61B 3/1225* (2013.01); *A61B 3/13* (2013.01); *A61B 3/145* (2013.01); *A61B 90/06* (2016.02); *A61B 90/37* (2016.02); *A61F 9/00736* (2013.01); *G02B 27/0101* (2013.01); *A61F 2009/00851* (2013.01); *A61F 2009/00863* (2013.01); *G02B 2027/0141* (2013.01)

(58) Field of Classification Search
CPC ......... A61B 3/102; A61B 90/06; A61B 90/37; A61B 3/1225; A61B 3/0025; A61B 3/0058; A61B 3/145; A61B 3/13; A61F 9/00736; A61F 2009/00851; G02B 27/0101
USPC ................................................. 351/206, 246
See application file for complete search history.

(56) References Cited

U.S. PATENT DOCUMENTS

| | | |
|---|---|---|
| 2007/0216909 A1 | 9/2007 | Everett et al. |
| 2014/0160264 A1 | 6/2014 | Taylor et al. |

OTHER PUBLICATIONS

PCT/IB2016/052516; International Search Report, International Searching Authority, dated Jul. 11, 2016, 4 pgs.

*Primary Examiner* — Jack Dinh

(57) ABSTRACT

An epiretinal membrane (ERM) visualization system includes an OCT system operable to generate an OCT image of a region of a patient's eye, the region of the patient's eye including an ERM. The ERM visualization system further includes an image processing unit operable to process the OCT image to identify the ERM by differentiating the ERM from other structures within the region of the patient's eye and generate an ERM map depicting one or more characteristics (including at least a location of a portion of the ERM within the region of the patient's eye) of the identified ERM. The ERM visualization system further includes a display operable to display the ERM map.

17 Claims, 4 Drawing Sheets

OPTICAL COHERENCE TOMOGRAPHY GUIDED EPIRETINAL MEMBRANE PEELING

FIELD

The present disclosure relates generally to improved visualization for ophthalmic surgeries and, more particularly, to optical coherence tomography guided epiretinal membrane peeling.

BACKGROUND

An epiretinal membrane (ERM) is a thin sheet of fibrous tissue that can form on the macula and may act like a film through which it is harder to see. The film may also contract like scar tissue, which can pull on the retina. ERM can cause various retinal pathologies, including retinal folds, retinal distortion, cystoids, macular edema, and small hemorrhages.

Currently, the only way to treat ERM is surgical removal through vitrectomy. In such a procedure, a vitreoretinal surgeon uses extremely fine forceps, under high magnification, to grasp and gently peel away the membrane from the retina (often referred to as "ERM peeling"). However, visualization of ERM may be difficult due to its thin and translucent nature, making ERM peeling a challenging procedure. One proposed technique to facilitate better visualization involves staining the ERM with vital dyes (e.g., Trypan Blue, ICG). However, the potential toxicity of these dyes to retina cells is still unclear and, as a result, this technique remains controversial.

Accordingly, there remains a need for improved visualization of ERM during an ERM peeling procedure. Certain embodiments of the present disclosure may address this need.

SUMMARY

In certain embodiments, an ERM visualization system includes an OCT system operable to generate an OCT image of a region of a patient's eye, the region of the patient's eye including an ERM. The ERM visualization system further includes an image processing unit operable to process the OCT image to identify the ERM by differentiating the ERM from other structures within the region of the patient's eye and generate an ERM map depicting one or more characteristics (including at least a location of a portion of the ERM within the region of the patient's eye) of the identified ERM. The ERM visualization system further includes a display operable to display the ERM map.

Certain embodiments of the present disclosure may provide one or more technical advantages. For example, because the transparent nature of ERM may make it difficult to locate, displaying an OCT-based ERM map to a surgeon may allow the surgeon to better visualize the location and characteristics of the ERM during an ERM peeling procedure. As a result, embodiments of the present disclosure may allow for more complete ERM removal while decreasing the risk of damage to the underlying structures of the patient's eye.

BRIEF DESCRIPTION OF THE DRAWINGS

For a more complete understanding of the present disclosure and the advantages thereof, reference is now made to the following description taken in conjunction with the accompanying drawings in which like reference numerals indicate like features and wherein.

Figure 1:
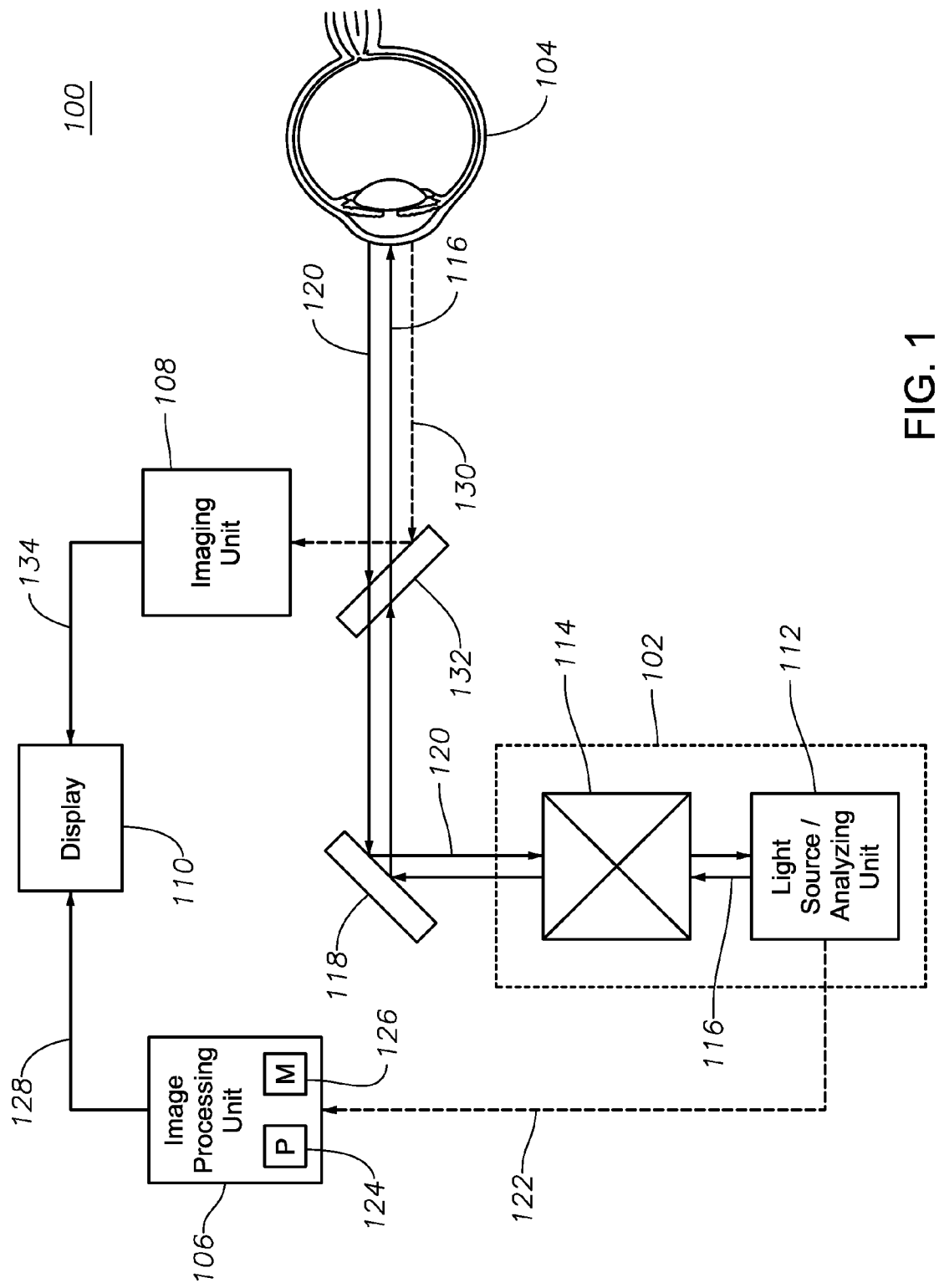
FIG. 1 illustrates an exemplary ERM visualization system facilitating OCT-guided ERM peeling, according to certain embodiments of the present disclosure.
Figure 2A:
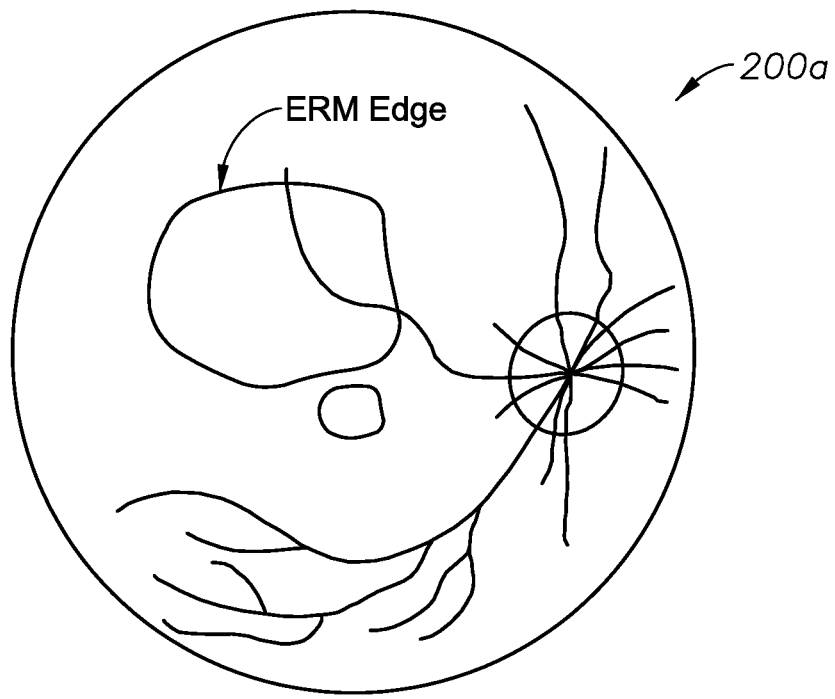
FIGS. 2A-2F illustrate exemplary ERM maps generated by the ERM visualization system depicted in FIG. 1, according to certain embodiments of the present disclosure.
Figure 2B:
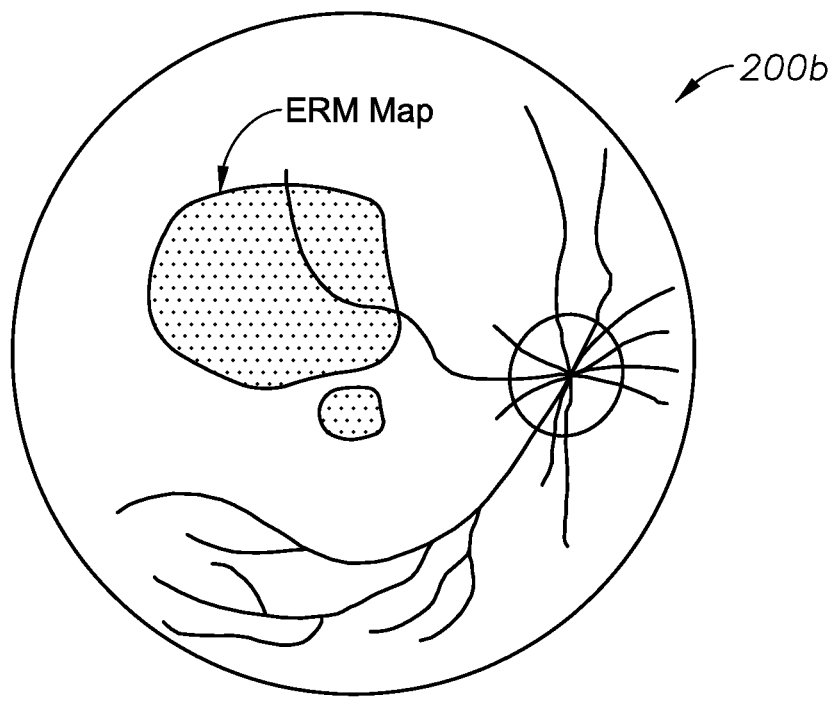
Figure 2C:
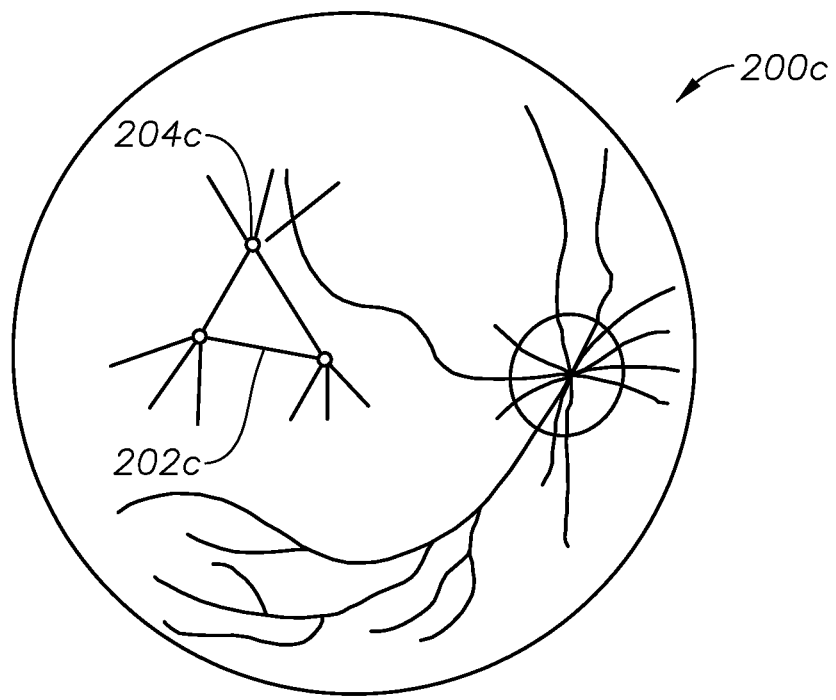
Figure 2D:
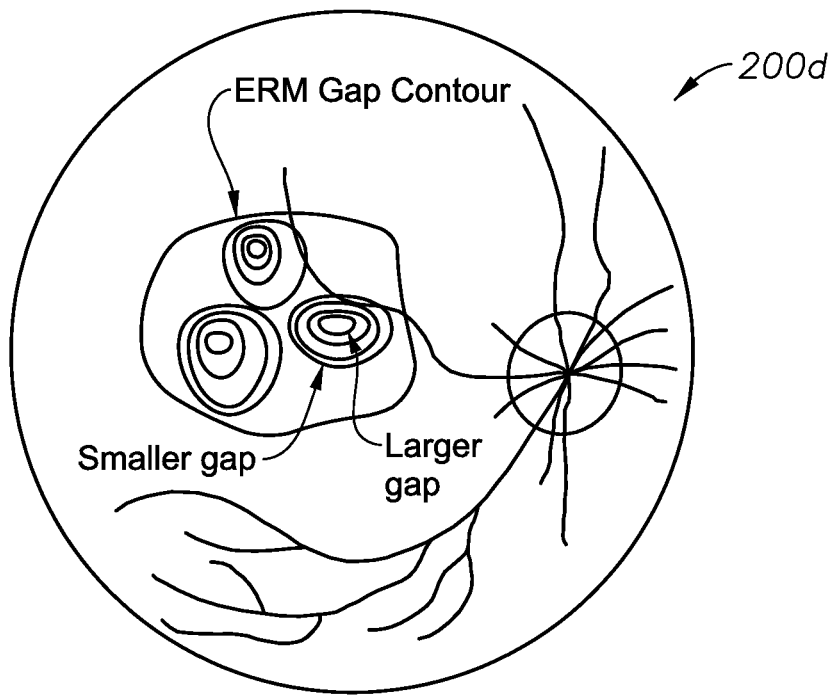
Figure 2E:
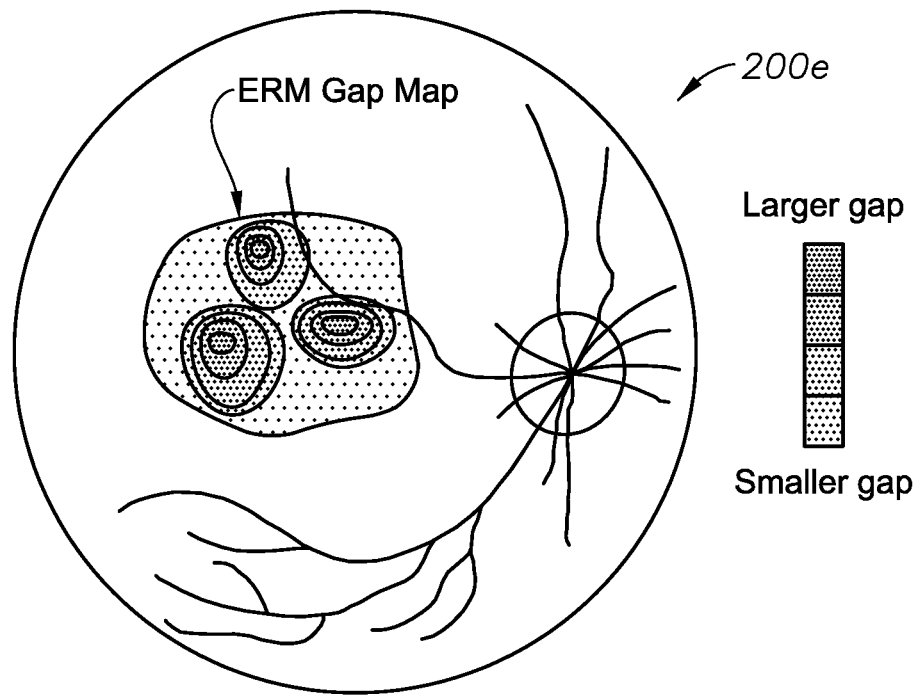
Figure 2F:
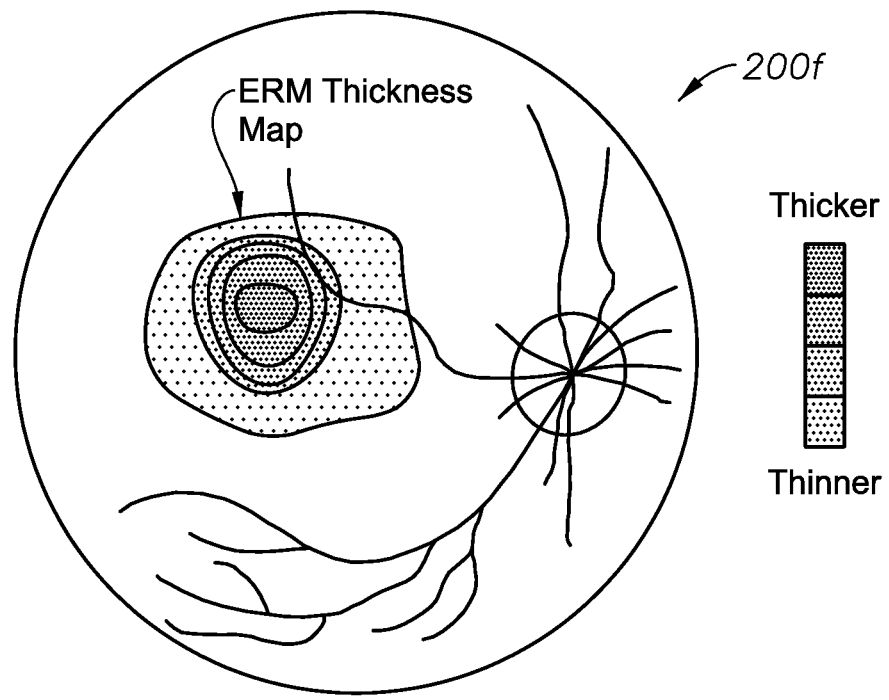

The skilled person in the art will understand that the drawings, described below, are for illustration purposes only. The drawings are not intended to limit the scope of the applicant's disclosure in any way.

DETAILED DESCRIPTION

For the purposes of promoting an understanding of the principles of the present disclosure, reference will now be made to the embodiments illustrated in the drawings, and specific language will be used to describe the same. It should nevertheless be understood that no limitation of the scope of the disclosure is intended. Any alterations and further modifications to the described systems, devices, and methods, and any further application of the principles of the present disclosure are fully contemplated as would normally occur to one skilled in the art to which the disclosure relates. In particular, it is fully contemplated that the systems, devices, and/or methods described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

In general, the present disclosure may provide an ERM visualization system that includes an OCT system operable to generate an OCT image of at least a portion of the eye (e.g., the area near the retina) and an image processing unit operable to process that OCT image to facilitate ERM visualization. For example, the image processing unit may process the OCT image to identify the location of the ERM, the thickness of the ERM, the gap between the ERM and the underlying structures of the eye, and/or contractions caused by the ERM. Based on this information, a display may be generated and displayed to a surgeon that includes an ERM map to guide the surgeon in performing an ERM peeling procedure.

FIG. 1 illustrates an exemplary ERM visualization system 100 facilitating OCT-guided ERM peeling, according to certain embodiments of the present disclosure. In general, ERM visualization system 100 includes an OCT system 102 for generating OCT images of a patient's eye 104 and an image processing unit 106 for processing the OCT image generated by OCT system 102 in order to determine characteristics of the ERM in the patient's eye 104. ERM visualization system 100 may further include an imaging unit 108 operable to generate images of the patient's eye during surgery and a display 110 for displaying an ERM map generated based on the characteristics of the ERM determined by image processing unit 106. For example, display 110 may display a video image of the patient's eye generated by imaging unit 108 along with an ERM map overlay including characteristics of the ERM determined based on the OCT image. As another example, display 110 may be a projection unit coupled to a surgical microscope (e.g., a heads-up-display) such that the ERM map may be displayed within the field of view of the surgical microscope.

Although the various components of system 100 are depicted and described as being part of a single system, the present disclosure contemplates that those components may be divided among any suitable number of systems, according to particular needs. As just one example, OCT system 102 and image processing unit 106 may each be part of a pre-operative imaging system, while imaging unit 108 and display 110 may be used during surgery (with the ERM map determined preoperatively imported, registered, and overlaid on the live image generated by imaging unit 108 and displayed on display 110).

OCT system 102 may include a light source/analyzing unit 112 and a beam scanner 114. In general, light source/analyzing unit 112 may generate an OCT imaging beam 116 and beam scanner 114 may direct the generated OCT imaging beam 116 to a particular region within the patient's eye 104. Reflections of the OCT imaging beam 116 from the particular region within the patient's eye 104 may return to light source/analyzing unit 112 along the same optical path as OCT imaging beam 116, and light source/analyzing unit 112 may generate OCT images of the particular region by determining interference between the reflections and a reference arm of the OCT imaging beam 116. The present disclosure contemplates that OCT system 110 may include any suitable additional optical components for manipulating OCT imaging beam 116 as would be understood by those of skill in the art, and those additional components are not depicted/described for the sake of simplicity.

In certain embodiments, the OCT imaging beam 116 may comprise a visible, an infrared, or near infrared light beam covering a relatively narrow band of wavelengths (e.g., 400 nm-700 nm, 830 nm-870 nm, 790 nm-900 nm, 950 nm-1150 nm). However, an OCT imaging beam 116 having any suitable spectral range may be used. The OCT imaging beam 116 may pass through beam scanner 114 (described in further detail below) along with any other suitable optical components of OCT system 102 (not depicted, as described above). OCT imaging beam 116 may then be directed to the patient's eye 104, such as by a mirror 118 operable to reflect light falling within the spectral range of the OCT imaging beam 116.

Beam scanner 114 may comprise any suitable optical component or combination of optical components facilitating focusing of the OCT imaging beam 116 in the X-Y plane. For example, beam scanner 114 may include one or more of a pair of scanning mirrors, a micro-mirror device, a MEMS based device, a deformable platform, a galvanometer-based scanner, a polygon scanner, and/or a resonant PZT scanner. In certain embodiments, the position of the optical components of beam scanner 114 may be manipulated in an automated manner. As just one example, beam scanner 114 may comprise a pair of scanning mirrors each coupled to a motor drive, the motor drives operable to rotate the mirrors about perpendicular axes. As a result, by controlling the position of the coupled motors (e.g., according to a predetermined or selected scan pattern), the X-Y positioning of OCT imaging beam 116 within the patient's eye 104 can be controlled. Additionally, the depth of focus of the OCT imaging beam 116 may be controlled by one or more other components of OCT system 102 as is understood in the art in order to facilitate 3-D OCT imaging.

A portion of the OCT imaging beam 116 reaching the patient's eye 104 may be reflected by the patient's eye (reflected OCT beam 120). Reflected OCT beam 120 may return to OCT system 102 along substantially the same optical path as traveled by OCT imaging beam 116. Once reflected OCT beam 120 reaches light source/analyzing unit 112, light source/analyzing unit 112 may construct an OCT image (A-scan) based on interference between the reflected OCT beam 120 and a reference arm of OCT imaging beam 116 (as is known in the art). Moreover, by moving the imaging beam in the X-Y plane via beam scanner 114 and/or changing the depth of focus of the imaging beam 114, a plurality of OCT images (A-scans) may be generated and combined into an OCT cross sectional image (B-scan), and a plurality of those cross sectional images (B-scans) may be combined to generate a 3-D OCT image.

The OCT image(s) generated by OCT system 102 (identified in FIG. 1 by reference numeral 122), which may include an A-scan, a B-scan, or a 3-D OCT image constructed by combining a plurality of B-scans as described above, may be communicated to image processing unit 106. In general, image processing unit 106 may analyze the received OCT images 122 to identify any ERM depicted in those images. Based on that analysis, image processing unit 106 may generate an ERM map to be displayed to a surgeon to assist in an ERM peeling procedure.

Image processing unit 106 may include any suitable combination of hardware, firmware, and software. In certain embodiments, image processing unit 106 may include a processing module 124 and a memory module 126. Processing module 124 may include one or more microprocessors, field-programmable gate arrays (FPGAs), controllers, or any other suitable computing devices or resources. Processing module 124 may work, either alone or with other components of ERM visualization system 100, to provide the functionality described herein. Memory module 126 may take the form of volatile or non-volatile memory including, without limitation, magnetic media, optical media, random access memory (RAM), read-only memory (ROM), removable media, or any other suitable memory component.

Image processing unit 106 may be programmed to (or may store software in memory module 126 that, when executed by processing module 124, is operable to) process the OCT images 122 generated by OCT system 102 to identify the location and/or characteristics of the ERM depicted in those images. For example, image processing unit 106 may process the OCT images 122 to differentiate ERM from the underlying structures of the eye (e.g., the retina). Because ERM may reflect OCT imaging beam 116 differently than the underlying structures, the ERM may be depicted differently in OCT images 122 (e.g., as a brighter region of the images) and thus may be differentiated from those underlying structures by image processing unit 106.

Having identified the ERM in the OCT images 122, image processing unit 106 may be further operable to construct an ERM map illustrating particular features of the ERM. For example, the ERM map may identify the edge of the ERM, contractions caused by the ERM, the thickness of the ERM, gaps between the ERM and the underlying structures of the eye, or any other suitable aspects of the ERM. Exemplary ERM maps are depicted in FIGS. 2A-2F, described in further detail below.

In certain embodiments, image processing unit 106 may be communicatively coupled (via wired or wireless communication) to display 110, and image processing unit 106 may communicate generated ERM maps (identified in FIG. 1 by reference numeral 128) to display 110 such that they may be displayed to a surgeon during an ERM peeling procedure. Display 110 may include any suitable display device, such as flat panel monitor operable to display still of live video images. For example, display 110 may display a live video image generated by imaging unit 108 with an overlaid ERM map 128 (as described in further detail below). Additionally or alternatively, display device 110 may include a projection unit coupled to the optics of a surgical microscope such that the ERM map may be displayed in the surgeon's field of view through the microscope.

In certain embodiments, ERM visualization system 100 may additionally include an imaging unit 108, which may include any suitable device for generating an image of a patient's eye 104. Additionally, imaging unit 108 may include any suitable magnification and focusing optics (not depicted) for generating any suitable image of the patient's eye. As a simplified example, visible or near infrared light 130 from the patient's eye 104 may be directed toward imaging unit 108 via a mirror 132 operable to reflect or partially reflect wavelengths in the visible or near infrared spectrum while allowing passage of OCT imaging beam 116 and reflected OCT beam 120. In certain embodiment, the generated images may be discrete still photographs of the patient's eye 104. In other embodiment, the generated images may comprise a continuous video stream of the patient's eye 104. Example imaging units may include digital video cameras, line scan ophthalmoscopes or confocal-scanning ophthalmoscopes.

In certain embodiments, imaging unit 108 may be communicatively coupled (via wired or wireless communication) to display 110, and imaging unit 108 may communicate generated images of the patient's eye 104 (identified in FIG. 1 by reference numeral 134) to display 110 such that they may be displayed to a surgeon. As described above, the ERM map 128 generated by image processing unit 106 may also be communicated to display 110 and overlaid on the image 134 generated by imaging unit 108. As one example, image 134 may be a live video image and ERM map 128 may be a static ERM map generated based on an earlier (pre-surgical or intra-surgical) OCT scan, the static ERM map 128 being displayed as overlaid on the relevant portion of live video image 134. Moreover, the static ERM map 128 may track the live video image 134 by correlating relevant structures of the eye 104 between the ERM map 128 and the live video image 134. In some embodiment, imaging unit 108 may communicate generated images of the patient's eye 104 directly to the image processing unit 106 to generate a combined or composite image with the ERM map information, which is then communicated to the display 110.

In certain embodiments, the displayed ERM maps 128 may be continuously or periodically updated during the ERM peeling procedure. For example, continuous OCT scanning may facilitate real-time updating of the ERM map (or a portion thereof) displayed via display 110. As another example, all or a portion of the original OCT image 122 may be updated periodically (e.g., in automated manner or at the surgeons request), resulting in corresponding updates to the generated ERM map 128. In either case, the original OCT image 122 may be updated only in the region in which the surgeon is working (e.g., by tracking the surgeon's instrument and imaging only an area surrounding the instrument), with corresponding updates to the ERM map 128 generated by image processing unit 106.

By displaying an ERM map to a surgeon (via display 110 or by projecting the ERM map into the surgical microscope, as described above), ERM visualization system 100 may facilitate better visualization of ERM during an ERM peeling procedure. As a result, ERM visualization system 100 may allow for more complete ERM removal while decreasing the risk of damage to the underlying structures of the patient's eye 104.

FIGS. 2A-2F illustrate exemplary ERM maps 200a-200f generated by ERM visualization system 100, according to certain embodiments of the present disclosure. In the illustrated embodiments, ERM maps 200a-200f are depicted as overlaid on a relevant portion of a fundus image generated by imaging unit 108, as discussed above.

More particularly, ERM map 200a (depicted in FIG. 2A) depicts the outline of the ERM edge, which may help a surgeon locate an appropriate starting point for ERM peeling procedure.

ERM map 200b (depicted in FIG. 2B) depicts the area in which the ERM is located in a semi-transparent manner, effectively providing a digital staining without the need to use dyes that may be toxic to the retina. Like the edge depicted in ERM map 200a, displaying ERM map 200b may help a surgeon locate an appropriate starting point for ERM peeling procedure.

ERM map 200c (depicted in FIG. 2C) depicts a contraction pattern 202c (with contraction centers 204c) caused by the ERM. The depicted contraction centers 204c may indicate locations where the ERM is tightly attached to the retina and may be high risk zones for the ERM peeling procedure.

ERM maps 200d and 200e (depicted in FIG. 2D and FIG. 2E, respectively) each illustrate gaps between the ERM and the underlying structures of the patient's eye (e.g., the retina). In particular, ERM map 200d represents the size of the gap using contour lines while ERM map 200d represents the size of the gap using shading. Because it may be desirable to begin the ERM peeling procedure at locations having a maximum gap between the EMR and the retina, ERM maps 200d and 200e may provide a useful guide in starting the ERM peeling procedure.

Finally, ERM map 200f (depicted in FIG. 2F) depicts the thickness of the ERM. Because it may be desirable to begin the ERM peeling procedure at locations having a maximum ERM thickness, ERM maps 200f may provide a useful guide in starting the ERM peeling procedure.

Although FIGS. 2A-2F illustrate alternative depictions of an ERM map, the present disclosure contemplates that those alternative depictions may be combined in any suitable manner. Moreover, the present disclosure contemplates that ERM visualization system 100 may be capable of generating each of the ERM maps depicted in FIGS. 2A-2F (or any suitable combination thereof) such that the surgeon may select a desired ERM map to be displayed.

It will be appreciated that various of the above-disclosed and other features and functions, or alternatives thereof, may be desirably combined into many other different systems or applications. It will also be appreciated that various presently unforeseen or unanticipated alternatives, modifications, variations or improvements therein may be subsequently made by those skilled in the art which alternatives, variations and improvements are also intended to be encompassed by the following claims.

What is claimed is:

1. An epiretinal membrane visualization system, comprising:
    an OCT system operable to generate an OCT image of a region of a patient's eye, the region of the patient's eye including an epiretinal membrane (ERM);
    an image processing unit operable to:
        process the OCT image to identify the ERM by differentiating the ERM from other structures within the region of the patient's eye; and
        generate an ERM map depicting one or more characteristics of the identified ERM, the one or more characteristics including at least a location of a portion of the ERM within the region of the patient's eye;

an imaging unit operable to generate a live video image of the region of the patient's eye during a surgical procedure; and a display operable to display the ERM map as an overlay on the image generated by the imaging unit, wherein the ERM map comprises a static ERM map registered and overlaid on the live video image.

2. The system of claim 1, wherein the OCT system is operable to generate the OCT image of the region of the patient's eye based at least in part on a portion of an OCT imaging beam reflected by the patient's eye.

3. The system of claim 1, wherein the display comprises a projection unit coupled to a surgical microscope, the projection unit operable to display the ERM map within the field of view of the surgical microscope.

4. The system of claim 3, wherein the projection unit is a heads-up display.

5. The system of claim 1, wherein:
the OCT system is further operable to generate an updated OCT image of a portion of the region of the patient's eye including the ERM; and
the image processing unit is further operable to:
process the updated OCT image to identify the ERM by differentiating the ERM from other structures within the region of the patient's eye; and
generate an updated ERM map by replacing a portion of the ERM map corresponding to the updated OCT image.

6. The system of claim 1, wherein the one or more characteristics of the identified ERM include an edge of the ERM.

7. The system of claim 1, wherein the one or more characteristics of the identified ERM include contraction caused by the ERM.

8. The system of claim 1, wherein the one or more characteristics of the identified ERM include a thickness of the ERM.

9. The system of claim 1, wherein the one or more characteristics of the identified ERM include a gap between the ERM and the underlying structures of the patient's eye.

10. A method, comprising:
generating an OCT image of a region of a patient's eye, the region of the patient's eye including an epiretinal membrane (ERM);
processing the OCT image to identify the ERM by differentiating the ERM from other structures within the region of the patient's eye;
generating an ERM map depicting one or more characteristics of the identified ERM, the one or more characteristics including at least a location of a portion of the ERM within the region of the patient's eye; and
generating a live video image of the region of the patient's eye during a surgical procedure; and
displaying the ERM map as an overlay on the image generated by the imaging unit, wherein the ERM map comprises a static ERM map registered and overlaid on the live video image.

11. The method of claim 10, the OCT image of the region of the patient's eye is generated based at least in part on a portion of an OCT imaging beam reflected by the patient's eye.

12. The method of claim 10, wherein displaying the ERM map comprises projecting the ERM map into the optics of a surgical microscope such that the ERM map is displayed within the field of view of the surgical microscope.

13. The method of claim 10, further comprising:
generating an updated OCT image of a portion of the region of the patient's eye including the ERM; and
processing the updated OCT image to identify the ERM by differentiating the ERM from other structures within the region of the patient's eye; and
generating an updated ERM map by replacing a portion of the ERM map corresponding to the updated OCT image.

14. The method of claim 10, wherein the one or more characteristics of the identified ERM include an edge of the ERM.

15. The method of claim 10, wherein the one or more characteristics of the identified ERM include contraction caused by the ERM.

16. The method of claim 10, wherein the one or more characteristics of the identified ERM include a thickness of the ERM.

17. The method of claim 10, wherein the one or more characteristics of the identified ERM include a gap between the ERM and the underlying structures of the patient's eye.

* * * * *